United States Patent [19]

Heavner et al.

[11] 4,331,595
[45] May 25, 1982

[54] IMMUNOREGULATORY DIKETOPIPERAZINE COMPOUNDS

[75] Inventors: George Heavner, Flemington; Foe-Siong Tjoeng, Neshanic Station; Gideon Goldstein, Short Hills, all of N.J.

[73] Assignee: Ortho Pharmaceutical Corporation, Raritan, N.J.

[21] Appl. No.: 248,758

[22] Filed: Mar. 30, 1981

Related U.S. Application Data

[62] Division of Ser. No. 162,228, Jun. 23, 1980, Pat. No. 4,289,759.

[51] Int. Cl.³ .......................................... C07C 103/52
[52] U.S. Cl. ............................................. 260/112.5 R
[58] Field of Search ................................. 260/112.5 R

[56] References Cited

U.S. PATENT DOCUMENTS

3,772,265  11/1973  Isowa et al. ................. 260/112.5 R
3,901,890   8/1975  Isowa et al. ................. 260/112.5 R

*Primary Examiner*—Delbert R. Phillips
*Attorney, Agent, or Firm*—Geoffrey G. Dellenbaugh

[57] ABSTRACT

Immunoregulatory 2,5-diketopiperazine compounds of formula:

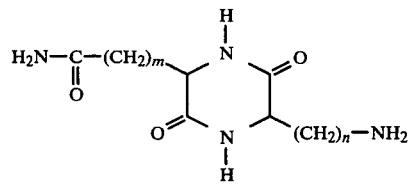

wherein m is 1 or 2 and n is 3 or 4 possess the ability to regulate the immune system of humans and animals. Administration of the compounds will return to a normal state an immune system in need of regulation.

1 Claim, No Drawings

IMMUNOREGULATORY DIKETOPIPERAZINE COMPOUNDS

This is a division of application Ser. No. 162,228, filed June 23, 1980, now U.S. Pat. No. 4,289,759.

BACKGROUND OF THE INVENTION

1. Field of the Invention

This invention relates generally to new immunoregulatory chemical compounds, therapeutic compositions containing the same, and methods for preparation and use thereof, and particularly to immunoregulatory diketopiperazines.

2. Description of the Prior Art

U.S. application Ser. No. 20,157, filed Mar. 14, 1979, in the name of two of the present applicants discloses a class of peptides having ubiquitin-like activity, which peptides contain a GLN-LYS fragment alone or in combination with various numbers of sarcosine amino acid residues. The application discloses that these peptides have the same activity as the long-chain polypeptide ubiquitin disclosed in U.S. Pat. No. 4,002,602. This patent and application are incorporated herein by reference.

Reference is made to this patent and patent application for a detailed discussion of other prior art and the biological processes involved in the present invention.

The present invention provides diketopiperazines (cyclic dipeptides) which also have potent ubiquitin-like activity. Since ubiquitin itself and the peptides disclosed in the referenced patent application are all linear, it is most surprising that the subject diketopiperazines, which are cyclic, possess this same utility.

SUMMARY OF THE INVENTION

It is therefore one object of this invention to provide new immunoregulatory diketopiperazines which are highly useful in the immune system of humans and animals. It is a further object to provide pharmaceutical compositions and methods employing these diketopiperazines as well as methods for preparing them.

Other objects and advantages of the invention will become apparent as the description proceeds.

In satisfaction of the foregoing objects and advantages, there is provided by this invention the novel 2,5-diketopiperazine compounds of formula:

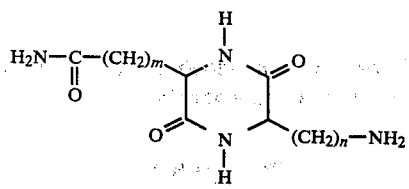

wherein m is 1 or 2 and n is 3 or 4. Also provided are therapeutic compositions containing these compounds, methods for preparation of these compounds, and methods for administration of these compounds to humans or animals for effecting biological actions thereon.

It will be apparent from an examination of the above formula that the subject compounds contain two asymmetric centers and can therefore exist in a variety of optically active forms. That is, the optically active centers may be both dextro (D), both levo (L), or one may be dextro and the other levo. All of these possible combinations of optical isomers are intended to be included within the subject invention.

The subject substituted diketopiperazines combine simplicity of structure, ease of manufacture, and high immunoregulatory potency, and thus provide significant advantages.

DETAILED DESCRIPTION OF THE INVENTION

As indicated above, this invention is concerned with new diketopiperazine compounds, therapeutic compositions containing these compounds, and methods for manufacture and use thereof.

In its broadest scope, the present invention provides 2,5-diketopiperazine compounds having the following formula:

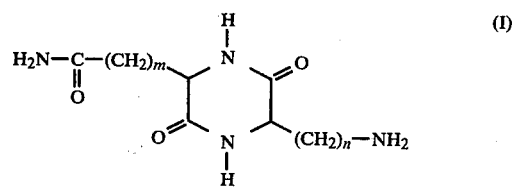

and optical isomers thereof, wherein m is 1 or 2 and n is 3 or 4.

Also included within the scope of the invention are the pharmaceutically acceptable salts of these compounds. As acids which are able to form salts with the compounds, there may be mentioned inorganic acids such as hydrochloric acid, hydrobromic acid, perchloric acid, nitric acid, thiocyanic acid, sulfuric acid, phosphoric acid, etc., and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid, and sulfanilic acid, for example.

It will be understood that the subject diketopiperazines may be viewed as cyclic dipeptides which may comprise as one of the amino acid constituents either D or L-glutamine or D- or L-asparagine; and as the other amino acid constituent either D- or L-lysine or D- or L-ornithine. The following are given as examples of cyclic dipeptides included within the generic formula given above: cyclo-(GLN-LYS), cyclo-(GLN-ORN), cyclo-(ASN-LYS), and cyclo-(ASN-ORN); cyclo-(D-GLN-D-LYS), cyclo-(D-GLN-D-ORN), cyclo-(D-ASN-D-LYS), and cyclo-(D-ASN-D-ORN); and cyclo-(D-GLN-LYS), cyclo-(GLN-D-LYS), cyclo-(ASN-D-LYS), cyclo-(GLN-D-ORN), cyclo-(D-ASN-ORN), and so forth.

In the above structures, the amino acid components of the cyclic dipeptides are identified by abbreviations for convenience. These abbreviations are as follows:

| Amino Acid | Abbreviation |
|---|---|
| L-glutamine | GLN |
| L-asparagine | ASN |
| L-lysine | LYS |
| L-ornithine | ORN |
| D-glutamine | D-GLN |
| D-asparagine | D-ASN |
| D-lysine | D-LYS |
| D-ornithine | D-ORN |

The subject compounds may be prepared by various techniques following principles generally known in the art. Synthesis of cyclic peptides is described, for example, in M. Bodanszky, et al., "Peptide Synthesis", Second Edition, 1976, and K. D. Kopple, "Synthesis of Cyclic Peptides", J. Pharm. Sci., 61 (9), 1345 (September 1972).

In this general scheme of preparation, the alpha-amino group of one of the constituent amino acids is protected on its alpha-amino group by allowing it to react with a reagent which will introduce a protecting group, as discussed further below. This protected constituent amino acid is then activated with respect to nucleophilic attack at its carboxy group by an amine, to form a carboxy activated protected constituent amino acid, as further described below. It is preferred that the constituent amino acid so treated is the glutamine or asparagine amino acid constituent.

The second constituent amino acid is then esterified on its carboxy terminus with, for example, a $C_1$-$C_6$ lower alkanol and (if appropriate) protected on its delta or epsilon amino group by allowing it to react with a reagent which will introduce a protecting group into that position. It is preferred that this amino acid constituent be lysine or ornithine.

Approximately molar equivalent amounts of each of these materials are allowed to react to form the resultant linear protected dipeptide, which is cyclized after removal of the alpha-amino-terminal protecting group. This cyclization may be accomplished by a variety of methods, including the active ester and azide methods and others well-known in the art. However, the direct method employing a carbodiimide (e.g., an N,N'-dialkylcarbodiimide, N,N'-dicyclohexylcarbodiimide, or N-ethyl-N'-(3-dimethylaminopropyl)carbodiimide, which is preferred, is illustrated below and employed in the Examples.

Finally, the delta or epsilon amino protecting group is removed, yielding the desired cyclic dipeptide as either a free base or acid addition salt.

This reaction scheme may be illustrated by the following, wherein m and n are as previously defined, X and Y are amino protecting groups, R is loweralkyl, and A is a carboxy activating group:

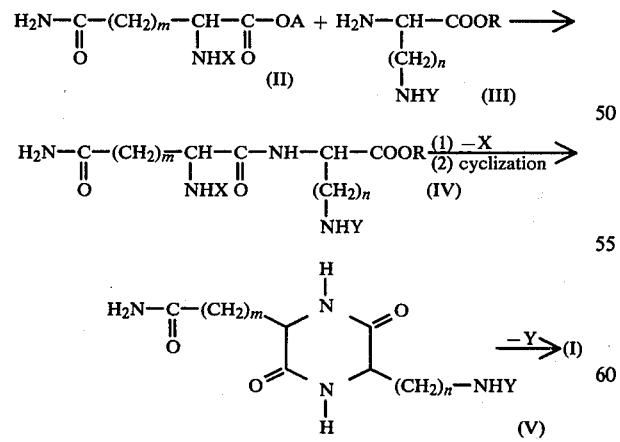

The amino protecting groups X and Y may be the same or different and should be stable to removal by the steps employed to join the two amino acids, while X should be removable under conditions which will not remove Y, and Y should be removable under conditions which will not destroy the resulting diketopiperazine compound.

Exemplary of suitable amino-protecting groups are those of formula:

wherein $R_1$ is aryl (such as phenyl, tolyl, or xylyl); adamantyl; monosubstituted methyl (such as allyl, beta-cyanoethyl, fluorenylmethyl, benzyl, or benzyl wherein the phenyl ring is substituted with from one to three members selected from halo, nitro, loweralkyl, and loweralkoxy); disubstituted methyl (such as diisopropylmethyl, diphenylmethyl, cyclohexyl, cyclopentyl, or vinyl); or trisubstituted methyl (such as t-butyl, t-amyl, dimethyltrifluoromethylmethyl, or dimethylbiphenylmethyl);

wherein $R_2$ is loweralkyl of two to four carbons such as ethyl, isopropyl, t-butyl, and the like, or loweralkyl of one to four carbons substituted with from one to five halo groups such as trifluoromethyl, chloromethyl, pentachloroethyl, and the like;

wherein V is S or O and $R_3$ and $R_4$ are each benzyl or loweralkyl;

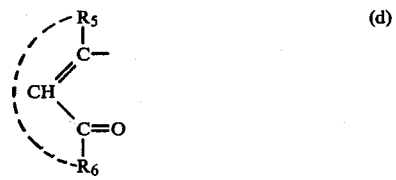

wherein $R_5$ and $R_6$ taken individually are each loweralkyl or $R_5$ and $R_6$ taken together is

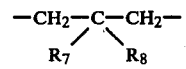

wherein $R_7$ and $R_8$ are each hydrogen or loweralkyl; and

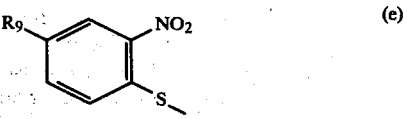

wherein $R_9$ is hydrogen or nitro;

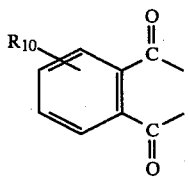 (f)

wherein $R_{10}$ is hydrogen, methyl, halo, or nitro.

As used herein, "halo" includes fluoro, chloro, bromo, and iodo, but chloro and bromo are preferred. The terms "loweralkyl" and "loweralkoxy" include, respectively, saturated aliphatic hydrocarbons of one to six carbons such as methyl, ethyl isopropyl, t-butyl, n-hexyl, and the like and the corresponding alkoxies such as methoxy, ethoxy, isopropoxy, t-butoxy, n-hexoxy, and the like. Methyl is the preferred loweralkyl and methoxy is the preferred loweralkoxy.

The reagents employed to introduce these protecting groups (usually the corresponding acid chlorides, although other derivatives may be used) are sometimes referred to herein as "protecting group reagents". Other suitable protective groups are disclosed in, for example, "Protective Groups in Organic Chemistry", J. F. W. McOmie, ed., Plenum Press, N.Y., 1973.

It is preferred that X be t-butyloxycarbonyl (BOC) and Y be benzyloxycarbonyl (CBZ).

A variety of reagents may be employed for producing the carboxy activated protected amino acid by introducing the A group.

One type of carboxy activated protected amino acid residue is a reactive ester. Exemplary of agents used to prepare the suitable active esters are phenol; phenol wherein the phenyl ring is substituted with one to five members selected from halo (e.g., chloro or fluoro), nitro, cyano, and methoxy; thiophenyl; N-hydroxyphthalimide; N-hydroxysuccinimide; N-hydroxyglutarimide; N-hydroxybenzamide; 1-hydroxybenzotriazole; and the like. Other suitable agents are disclosed in, for example, "Protective Groups in Organic Chemistry", J. F. W. McOmie, ed., referred to above. The specific examples provided below employ ortho-nitrophenol.

Other activation methods, such as the mixed or symmetrical anhydride method, the acid chloride method, and the azide method, are well-known in the art, being described in, e.g., Bondanszky et al., "Peptide Synthesis", 2nd ed., 1976, pp 85-128. These other methods may also be employed.

The subject compounds exhibit immunoregulatory activity as demonstrated in an in vitro cytotoxic lymphocyte precursor unit (CLP-U) assay, in which the effect of in vitro incubation of one of the subject compounds with mouse spleen cells on the generation of CLP-U was evaluated. This assay correlates directly with immune response in warm-blooded animals, including humans. That is, if a tested compound stimulates or inhibits the CLP-U generated in the assay at a certain concentration, these results indicate the immunoregulatory effect of the tested compound. This assay has also been conducted, e.g., for the known immunoregulatory peptide TP5, which has confirmed this correlation. For a more detailed description of this assay and its use for measuring immune regulation, reference is made to C. Y. Lau and G. Goldstein, J. Immunology: 124 (4), 1861-1865 (April 1980), which is incorporated herein by reference.

Because of these characteristics of the subject compounds, they are therapeutically useful in the treatment of humans and animals since they have the capability for correcting immune deficiencies in subjects in need of such correction. As a result, the products of this invention are considered to have multiple therapeutic uses. Because of their biological characteristics, which are extremely active at low concentrations, they are considered useful in assisting the collective immunity of the body in that the compounds will increase or assist in therapeutic stimulation of cellular immunity and thereby become useful in the treatment of diseases involving chronic infection in vivo, such as fungal or mycoplasma infections, tuberculosis, leprosy, acute and chronic viral infections, and the like. Further, the compounds are considered to be useful in any area in which cellular immunity is an issue and particularly where there are deficiencies in immunity such as in the DiGeorge Syndrome (congenital absence of thymus). Also, where there is an excess of antibody production, the compounds can correct this condition by regulating T cell production. Thus, they may be of therapeutic use in certain autoimmune diseases in which damaging antibodies are present, for example, systemic lupus erythematosus, rheumatoid arthritis, and the like. Further, because of the characteristics of the compounds, they have in vitro usefulness in inducing the development of surface antigens of T cells, in inducing the development of the functional capacity to achieve responsiveness to mitogens and antigens and cell collaborativity in enhancing the ability of B cells to produce antibodies. Still further, the compounds are useful in treatment of conditions such as neoplasia in which the immune response is subnormal. Administration of an effective immunoregulatory amount of the subject compounds will assist in the treatment of such conditions (and especially neoplasia) either alone or in adjunct with other forms of treatment such as surgical removal.

One aspect of the present invention is therefore a method for regulating the immune system of a subject, human or animal, in need of such immune regulation which comprises administration to said subject an effective immunoregulatory amount of one of the subject compounds, preferably in admixture with a pharmaceutical carrier. As used therein, the term "regulate" means that the subject compounds cause the immune system to return from an abnormal, diseased state to a normal, balanced state.

A further important property of the compounds of this invention is that they are highly active in very low concentrations ranging from 0.1 pg/ml. The carrier may be any of the well-known carriers for this purpose including normal saline solutions, preferably with a protein diluent such as bovine serum albumin (BSA) to prevent adsorptive losses to glassware at these low concentrations. The compounds of this invention are active parenterally at about 1 ng/kg of body weight. For the treatment of rheumatoid arthritis, they may generally be administered at a rate of about 0.1 to 100 ng/kg of body weight. Generally, the same range of dosage amounts may be used in treatment of the other conditions or diseases mentioned.

To prepare the pharmaceutical compositions of the present invention, a compound of Formula (I) or an acid addition salt thereof is combined as the active ingredient in intimate admixture with a pharmaceutical carrier according to conventional pharmaceutical compounding techniques, which carrier may take a wide variety of forms depending on the form of preparation desired for administration, e.g., sublingual, rectal, nasal, oral, or parenteral. In preparing the compositions in oral dosage form, any of the usual pharmaceutical media may be employed, such as for example, water, glycols, oils, alcohols, flavoring agents, preservatives, coloring agents, and the like in the case of oral liquid preparations such as for example, suspensions, elixirs, and solutions; or carriers such as starches, sugars, diluents, granulating agents, lubricants, binders, disintegrating agents, and the like in a case of oral solid preparations, such as for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients, for example, to aid solubility or for preservative purposes, may be included. Injectable suspensions may also be prepared, in which case appropriate liquid carriers, suspending agents, and the like may be employed. The parenteral pharmaceutical compositions of the invention should be designed to administer the subject compounds at a rate of about 0.1 to about 100 ng/kg of body weight. The oral compositions should administer about 100 to 1000 times the dose for parenteral administration—i.e., from about 10 ng/kg to about 100 μg/kg of body weight. Accordingly, the parenteral compositions should contain, per dosage unit, from about 5 ng to about 5 μg, whereas the oral compositions should contain, per dosage unit, from about 500 ng to about 5 mg of the subject compound.

The preparation and evaluation of an exemplary compound of the invention is given below for purposes of illustration. Unless otherwise stated, all parts are by weight.

EXAMPLE I

$N^\alpha$-BOC-L-Glutaminyl-$N^\epsilon$-Benzyloxycarbonyl-L-Lysine-OMe

BOC-Gln-ONp (3.67 g; 0.01 moles) and $N^\epsilon$-Z-Lys-OMe.HCl (3.64 g; 0.011 moles) were dissolved in 30 ml of DMF. The mixture was cooled in an ice bath and diisopropylethylamine (1.91 ml; 0.011 moles) was added slowly with stirring. The reaction was stirred for 3 days at ambient temperature. The solvent was removed under reduced pressure and the residue was redissolved in ethylacetate (200 ml) and washed with 10% sodium bicarbonate solution (6×50 ml), $H_2O$ (3×50 ml), 0.1 N HCl (3×50 ml) and $H_2O$ (3×50 ml). The organic layer was dried over sodium sulfate and after filtration, the solvent was removed under reduced pressure. The crude product (4.6 g) was obtained by adding ether to the mixture, removing the solid by filtration, washing with ether and drying in vacuo. This material was suspended in ethylacetate, filtered and washed with minimum amount of ethylacetate. The product was dried in vacuo to give a white solid (3.8 g, 73% of yield), m.p. 99°–100° C.; Rf 0.49 ($CHCl_3$/MeOH/HOAc=85:10:5; Silica Gel GF 250 microns); pmr ($CD_3OD$) δ, 1.42 [s, 9H, $(CH_3)_3C$—], 1.5–2.4 (M, 10H, methylene H), 3, 1 (t, 2H, $CH_2$—NH—Z), 3.7 (s, 3H, —$OCH_3$), 4–4.5 (m, 2H, α—CH—), 5.1 (s, 2H, —$CH_2$—$C_6H_5$), 7.39 (s, 5H, —$C_6H_5$).

Anal. Calcd. for $C_{25}H_{38}N_4O_8$: C, 57.46; H, 7.33; N, 10.71. Found: C, 57.23; H, 7.24; N, 10.52.

EXAMPLE II cyclo-(L-Glutaminyl-$N^\epsilon$-Benzyloxycarbonyl-L-Lysine)

BOC-Gln-$N^\epsilon$-CBZ-Lys-OMe (2.15 g; 4.11 mmoles) was treated with 10 ml of 4 N HCl/Dioxane for 1 h at room temperature. The solvent was removed under reduced pressure and the residue was dissolved in 25 ml of $CH_2Cl_2$. The solution was cooled down to 0° C. and diisopropylethylamine (0.96 ml; 4.11 mmoles) was added slowly under stirring. The mixture was taken down to dryness and the remaining material was dissolved in 50 ml of $CH_3OH$ and refluxed gently for 24 h. The mixture was placed in the cold room and the precipitate was collected by filtration and washed with water thoroughly. The product was dried in vacuo to give a white solid, (300 mg; 24% of yield); m.p. 235° C.; a second crop of material was obtained (400 mg; 26% of yield); Rf 0.256 (n-Butanol/$H_2O$/HOAc=3:1:1, Silica Gel GF, 250 microns); pmr (TFA) δ, 1.4–2.8 (m, 12H, methylene H), 4.2–4.5 (m, 2H, α—CH), 5.2 (s, 2H, —$CH_2$—$C_6H_5$); 7.32 (s, 5H, —$C_6H_5$).

Anal. Calcd. for $C_{19}H_{26}N_4O_5$: C, 58.45; H, 6.71; N, 14.34. Found: C, 58.31; H, 6.61; N, 14.30.

EXAMPLE III cyclo-(L-Glutaminyl-L-lysine).Hydrochloride cyclo-(L-Gln-$N^\epsilon$-Benzyloxycarbonyl-L-Lys) (140 mg; 0.48 mmoles) was suspended in 10 ml of acetic acid and 10 ml of 1 N HCl. To the suspension, 100 mg of 10% Pd/C was added slowly. The mixture was hydrogenated on a Parr-shaker at 40 psi for 24 h. The catalyst was removed by filtration catalyst was removed by filtration and the filtrate was taken down to dryness. To the residue was added 15 ml of ethanol and few drops of water. The mixture was placed in the cold room overnight and the precipitate was collected by filtration and dried in vacuo. The yield was 95% (57 mg, 1st crop and 40 mg, 2 nd crop); m.p. 246°–248° C. Rf 0.20 (n-Butanol/HOAc/$H_2O$=3:1:1, Silica Gel GF, 250 microns); M.S. (probe): m/e 256 ($M^+$); pmr ($D_2O$) δ 1.3–2.4 (m, 10H, methylene H), 2.8–3.1 (m, 2H, —$CH_2$—NH 4.05 (t, 2H, α—CH—).

Anal. Calcd. for $C_{11}H_{20}N_4O_3$: C, 45.13; H, 7.23; N, 19.13. Found: C, 45.42; H, 7.10; N, 18.41.

EXAMPLE IV

To evaluate the immunoregulatory activity of the cyclic dipeptide produced in Example III, the following assay was conducted.

Single cell suspensions were made from the spleens of normal C57BL/6 mice (female, 8 week old, Jackson Laboratory, Bar Harbour, Maine) and the cells were washed three times with PBS. The cells were then resuspended in RPMI 1640 medium (Gibco) and then incubated with various concentrations of the test peptide for 1 h at 37° C. After incubation, the cells were washed and the frequency of CLP-U was estimated by the limiting dilution assay according to the method of Teh, et al., J. Immunol. 118:1049(1977) and Lindahl and Wilson, J. Exp. Med. 145:508(1977).

Limiting numbers of C57BL/6 spleen cells ($2 \times 10^4$ to $8 \times 10^4$) were put in V-bottom Linbro trays (Flo Laboratories) together with mitomycin-C-treated DBA spleen cells (DBA/2J mice, Jackson Laboratory, Bar Harbour, Maine), $10^7$ DBA cells having been treated with 30 μg of mitomycin-C for 30 minutes at 37° C. The number of DBA cells used varied from $1.2 \times 10^5$ to $6.5 \times 10^5$ per culture. Twenty replicates were set up for each cell concentration.

The combined cultures were then incubated at 37° C. for six days, at the end of which period 100 μl of the supernatant medium was removed from each well, and the cells were then mixed with 0.1 ml of fresh medium containing $2 \times 10^4$ P815 mastocytoma cells labelled with $^{51}Cr$ as described previously by Teh, et al. After a further incubation period of 4 h, 100 μl of the supernatant fluid in each well was removed and the radioactivity therein was determined in a gamma spectrometer. The background chromium release from cultures containing only C57BL/6 cells or only DBA cells was always less than 15%.

The frequencies of CLP-U were calculated according to Poisson's statistics as follows. First, the mean spontaneous release was calculated by averaging the counts of twenty wells that received only C57BL/6 cells. Wells were scored as positive if their counts were greater than 2.07 standard deviations above this mean spontaneous release value ($P<0.05$). According to Poisson's distribution, the frequencies of precursors can then be calculated by the equation $P=E^{\delta N}$ where P equals the probability of response, $\delta$ equals frequency, and N equals the number of cells put in the culture.

The percent of non-responding cultures for each C57BL/6 concentration was calculated and plotted on semi-logarithmic scale as a function of the cell concentration. According to the equation given above, the inverse of the number of cells in culture that will give 37% non-responding culture is the frequency of precursors in that culture. The best fit regression line by least square method was calculated for each line and the frequency was then estimated.

Enhancement of CLP-U upon suboptimal stimulation was observed for the cyclic dipeptide of Example III at concentrations ranging from 0.1 pg/ml through 10 ng/ml, although optimal enhancement was observed from 0.1 pg/ml through 0.01 ng/ml.

EXAMPLE V

Following the procedures of Examples I–III, but substituting for the reagents used therein equivalent amounts of suitable starting materials, there are prepared the following: cyclo-(GLN-LYS), cyclo-(GLN-ORN), cyclo-(ASN-LYS), cyclo-(ASN-ORN), cyclo-(D-GLN-D-LYS), cyclo-(D-GLN-D-ORN), cyclo-(D-ASN-D-LYS), cyclo-(D-ASN-D-ORN), cyclo-(D-GLN-LYS), cyclo-(GLN-D-LYS), cyclo-(ASN-D-LYS), cyclo-(GLN-D-ORN), and cyclo-(D-ASN-ORN).

These compounds also possess immunoregulatory activity as demonstrated by the test of Example IV.

The above Examples have been given by way of illustration and not to limit the scope of the present application, which scope is determined only by the following claims.

We claim:

1. A method of preparing a chemical compound of formula:

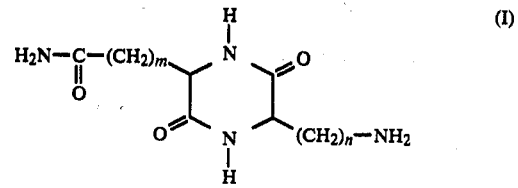

wherein m is 1 or 2 and n is 3 or 4 which comprises:
(a) reacting approximately molar equivalents of a compound of formula:

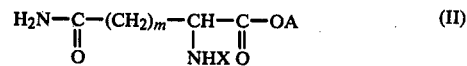

and a compound of formula:

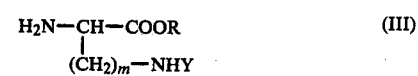

to form a compound of formula:

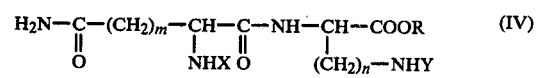

(b) removing the X protecting group from compound (IV)
(c) cyclizing the resultant compound to form a compound of formula:

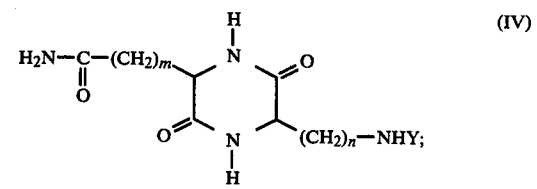

and
(d) removing the Y protecting group from compound (V), whereby compound (I) is formed;
wherein:
X and Y are each selected from the group consisting of:

wherein $R_1$ is phenyl; tolyl; xylyl; adamantyl; allyl; beta-cyanoethyl; fluoroenylmethyl; benzyl, benzyl wherein the phenyl ring is substituted with from one to three members selected from halo, nitro, loweralkyl, and loweralkoxy, diisopropylmethyl; diphenylmethyl; cyclohexyl; cyclopentyl; vinyl; t-butyl; t-amyl, dimethyltrifluoromethylmethyl; or dimethylbiphenylmethyl;

wherein R₂ is loweralkyl of two to four carbons or loweralkyl of one to four carbons substituted with from one to five halo groups;

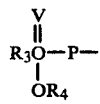 (c)

wherein V is S or O and R₃ and R₄ are each benzyl or loweralkyl;

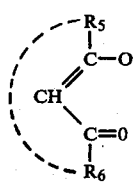 (d)

wherein R₅ and R₆ taken individually are each loweralkyl or nd R₅ and R₆ taken together is

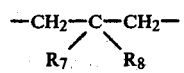

wherein R₇ a R₈ are each hydrogen or loweralkyl;

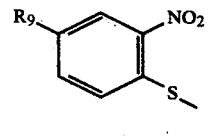 (e)

wherein R₉ is hydrogen or nitro; and

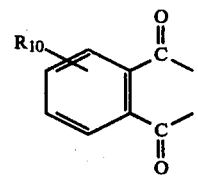 (f)

wherein R₁₀ is hydrogen, methyl, halo, or nitro; and

A is benzyl or benzyl in which the phenyl group is substituted with from one to three members each selected from halo, nitro, C₁-C₃ loweralkyl, and C₁-C₃ loweralkoxy.

* * * * *